United States Patent [19]
Grossman

[11] Patent Number: 5,788,488
[45] Date of Patent: Aug. 4, 1998

[54] DENTAL REAMER STOP DISPENSER

[75] Inventor: Sanford Grossman, Canoga Park, Calif.

[73] Assignee: Precision Dental International, Inc., Canoga Park, Calif.

[21] Appl. No.: 700,350

[22] Filed: Sep. 23, 1996

[51] Int. Cl.⁶ ............................................. A61C 1/14
[52] U.S. Cl. ........................ 433/49; 433/102; 221/288
[58] Field of Search ................... 433/49, 102; 221/288, 221/289

[56] References Cited

U.S. PATENT DOCUMENTS

| | | | |
|---|---|---|---|
| 2,149,445 | 3/1939 | Kreiten | 221/289 |
| 3,874,564 | 4/1975 | Huneke | 221/288 |
| 3,964,170 | 6/1976 | Zdarsky | 33/169 B |
| 4,557,690 | 12/1985 | Randin | 433/49 |

Primary Examiner—John J. Wilson
Attorney, Agent, or Firm—Welsh & Katz, Ltd.

[57] ABSTRACT

An apparatus is provided for dispensing washers for controlling a depth a penetration of a reamer during root canals. The apparatus has a body including a recess for storing a number of washers to be positioned on the reamer. The body also has a washer access door with an aperture, mounted on said body. The recess within the body has oppositely disposed side walls which converge to a notch at a location proximate said access door and top and bottom walls bounding said notch. The top wall has a passageway and aperture formed in said top wall above said notch for receiving said access door within the passageway between the top wall and recess, the access door being slidably movable between a first position in which the aperture of the top wall and aperture of the access door are in registration with the notch to permit a washer within the notch to be engaged by said reamer, and a second position.

16 Claims, 2 Drawing Sheets

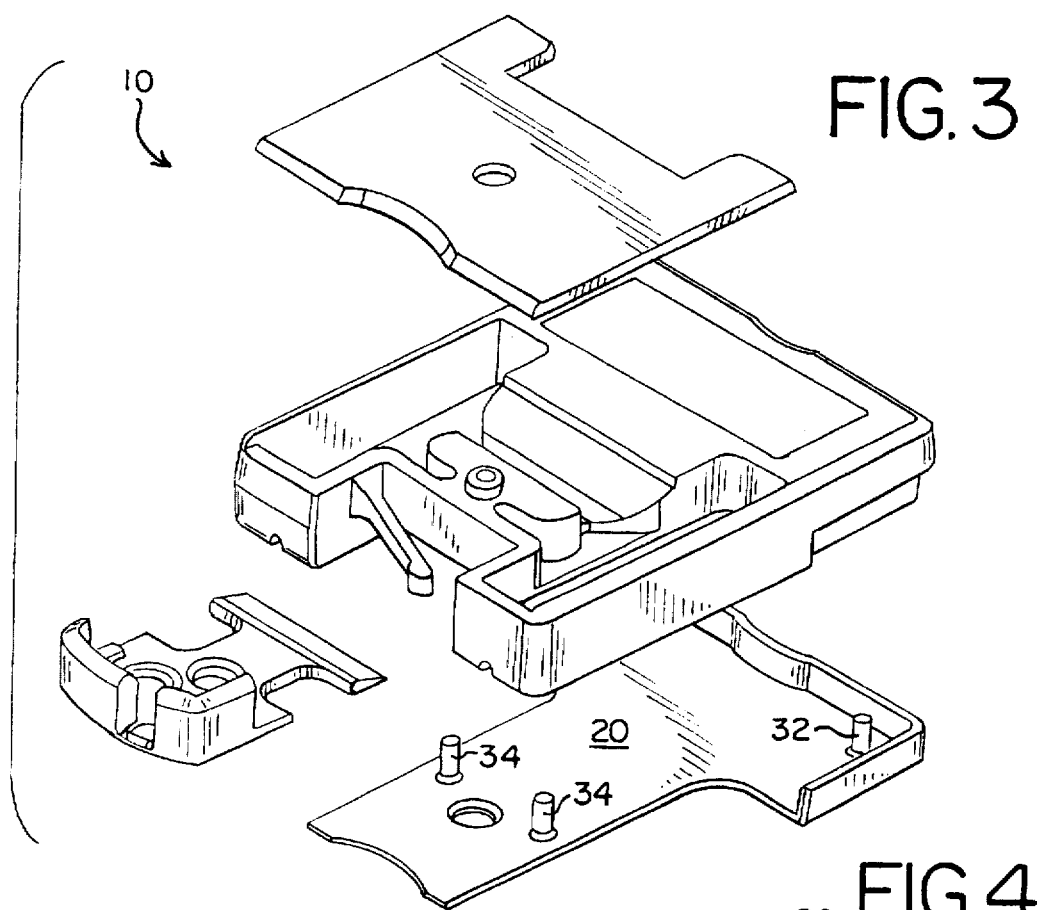
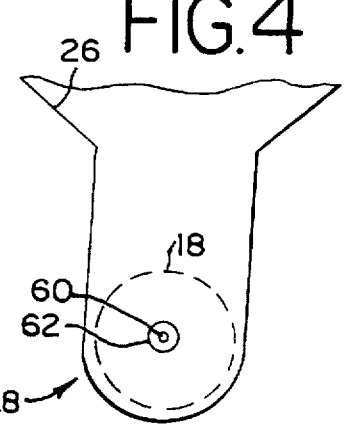
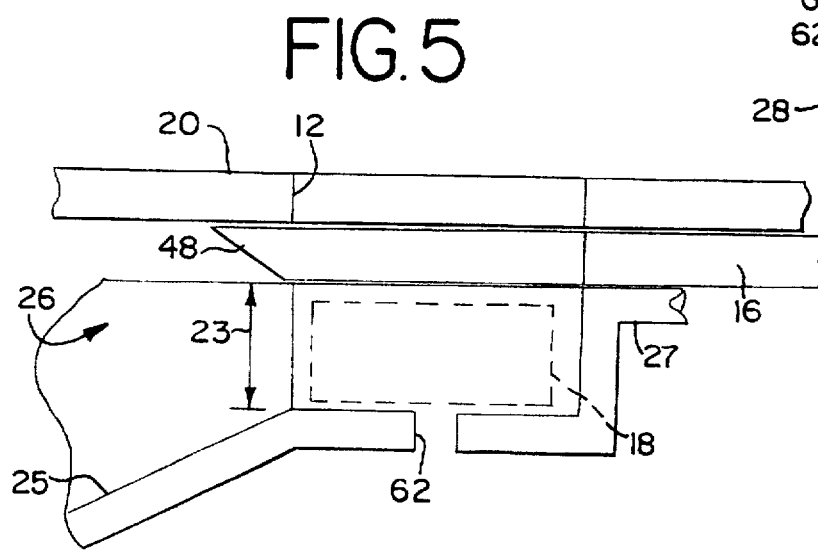

5,788,488

DENTAL REAMER STOP DISPENSER

FIELD OF THE INVENTION

The field of the invention relates to dental reaming devices and more particularly to dental washers used as stops on endodontic instruments during root canals.

BACKGROUND OF THE INVENTION

The benefits of root canals for the treatment of tooth abscesses are well known. The use of dental reamers for doing root canals is also generally known.

The use of a reamer, however, is complicated by the difficulty of knowing when the hole created by the reamer is of sufficient depth. If a hole created by a reamer is of insufficient depth, the root canal will be ineffective, resulting in continued suffering and discomfort for the dental patient.

If the hole is too deep, the reamer may protrude through the root of the tooth, possibly endearing the jawbone. The entry of a reamer into the jawbone of a dental patient could lead to numerous complications including pain, infections and possibly lawsuit.

As a means of avoiding the possibility of a reamer penetrating too deeply into a tooth, thin polymeric dental washers (e.g., silicone) are often disposed on a reamer as a marker to indicate a desired depth of tooth penetration. To use a silicone washer, the reamer is simply pressed through the center of the washer to a desired depth. Pressing the reamer through the washer secures the washer to the reamer in a manner such that the dentist can use the washer as a gauge of reamer penetration.

While dental washers have provided an effective means of gauging reamer depth, the handling of such dental washers is difficult. The diameter of such washers is often less than 3/16 inch and less than 1/16 inch thick. Because of such small size, the ability of a dentist to grasp and pick up a dental washer is limited. Further, even if a dentist is successful in picking up a washer, he must still push the reamer through the washer without impaling his own finger.

Accordingly, it is an object of this invention to provide a dispenser for dental washers that avoids the problems of handling such washers.

It is a further object of the invention to provide a dispensing device which singulates the dental washers to a location where they may be directly engaged by a reamer without manual intervention.

It is a further object of the invention to dispense the dental washers from a container that maintains the hygienic integrity of the washers until use.

SUMMARY OF THE INVENTION

An apparatus is provided for dispensing washers for controlling a depth a penetration of a reamer during root canals. The apparatus has a body including a recess for storing a number of washers to be positioned on the reamer. The body also has a washer access door with an aperture, mounted on said body. The recess within the body has oppositely disposed side walls which converge to a notch at a location proximate said access door and top and bottom walls bounding said notch. The top wall has a passageway and aperture formed in said top wall above said notch for receiving said access door within the passageway between the top wall and recess, the access door being slidably movable between a first position in which the aperture of the top wall and aperture of the access door are in registration with the notch to permit a washer within the notch to be engaged by said reamer, and a second position.

BRIEF DESCRIPTION OF THE DRAWINGS

FIG. 3 is an exploded bottom view of the dispenser of FIG. 1;

FIG. 4 is a top view of a dispensing notch of the dispenser of FIG. 1; and

FIG. 5 is a cut-away side view of the dispensing notch of the dispenser of FIG. 1.

DETAILED DESCRIPTION OF A PREFERRED EMBODIMENT

Figure 1:
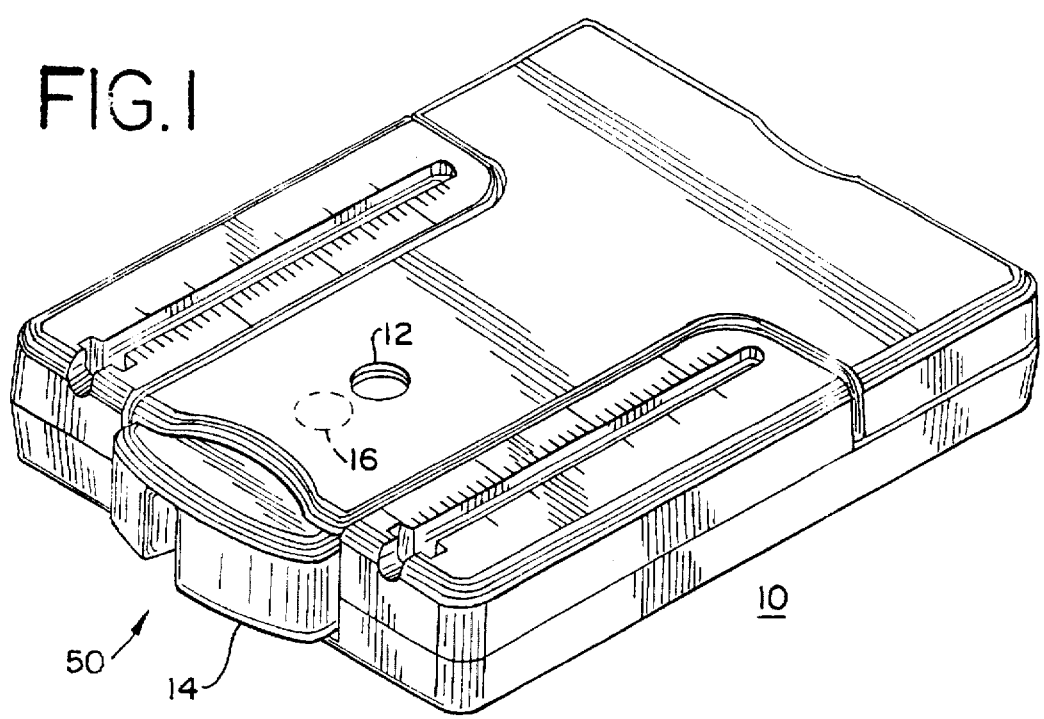
FIG. 1 is a side perspective view of the dental washer dispenser in accordance with an embodiment of the invention.

FIG. 1 is a perspective view of a dispenser 10 for dental washers, generally, under an embodiment of the invention. Included within the dispenser 10 is a hole 12 for insertion of a reamer for penetrating and engaging a dental washer. Also shown in FIG. 1 is a tab (access gate 14) which may be activated by a user (not shown) to clear the hole 12, thereby allowing access to the dental washers.

Figure 2:
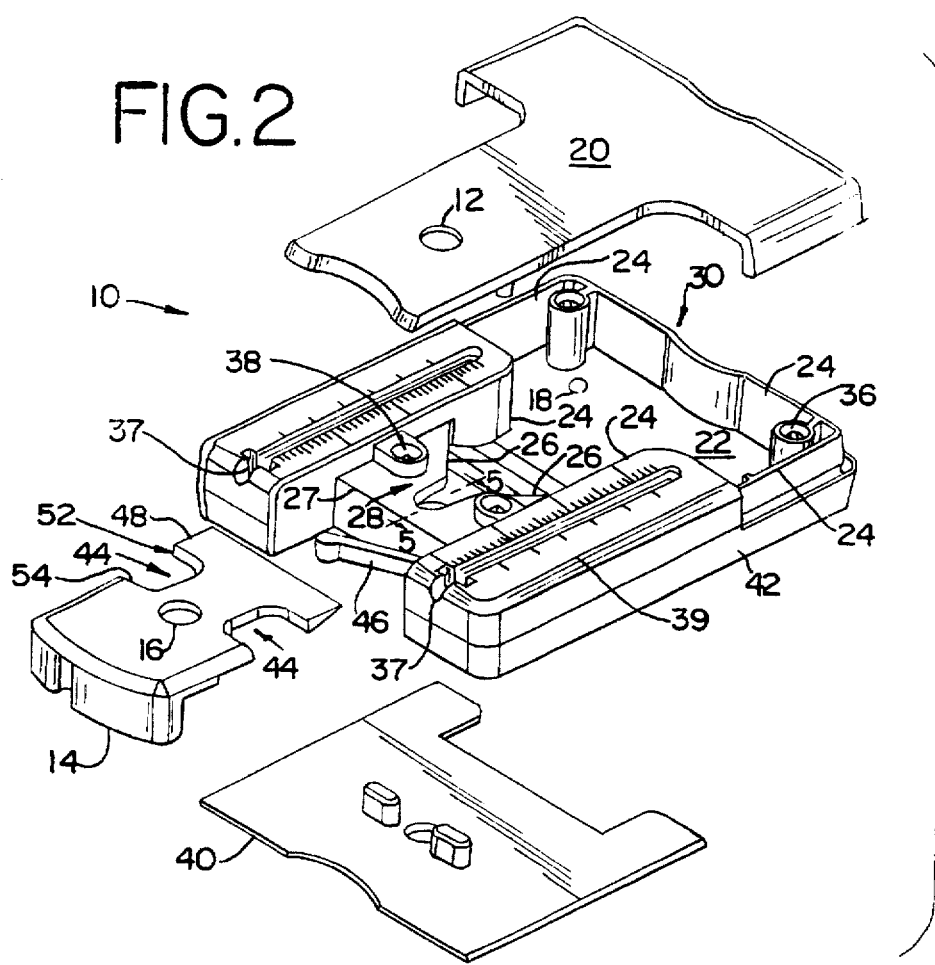
FIG. 2 is an exploded top view of the dental washer dispenser of FIG. 1.

FIG. 2 is an exploded view of the dispenser 10 of FIG. 1. As shown, the dispenser 10 includes at least four parts: 1) a top plate 22; 2) a base 42; 3) the access gate 14; and 4) a bottom cover plate 40. Taking the base 42 first, the base 42 includes a bottom plate 22 and side walls 24. The side walls 24, along with the bottom plate 22 and top plate 20 define a recess 30 for containing dental washers 18 (one of which is shown within the recess 30). The side walls 24 trace a path along a portion of the periphery of the bottom plate 22 from the back to the front and converge along a converging portion 26 to form a notch 28 in the side walls.

FIG. 4 is an enlarged view of the notch 28. The notch 28 may form a semicircle at its tip with a center axis of the semicircle and notch shown generally at 60. The radius of the semicircle is chosen to be slightly larger than that of a washer 18 (shown in phantom in FIG. 4). A small hole 62 is bored coaxial with the center axis 60 of the semicircle of a size slightly larger that the reamer. The hole 62 allows the reamer to be pushed (pricked) through the washer 18 and into the hole 62 to advance the washer 18 to an appropriate location along the length of the reamer. Gauges 37 on an outer shoulder of the dispenser 10 are used to precisely position the washer 18 on the reamer.

FIG. 5 is side, cut-away view of the notch 28. As shown, a depth 23 of the notch 28 is chosen to be slightly greater than the thickness of the washer 18. Further, while the side walls 26 converge into the notch, the bottom plate 22 also slopes upward within a sloping area 25 to provide a depth 23 within the notch of slightly more than a washer 18.

FIG. 3 shows an exploded view of the dispenser 10 from a bottom perspective. The top plate 20 has a bottom set of posts 32 (one of which is shown in FIG. 3) and a front set of posts 34. The top plate 20 attaches to the base 42 via engagement of the rear posts 32 to a rear set of sockets 36 and the front posts 34 to the front sockets 38 of the base 42. Upon engagement of the top plate 20 to the base 42 the hole 12 in the top plate 20 is in coaxial registration with the center of the notch 28.

The access gate 14 is formed to be interleaved between the top plate 20 and a support plate 27, between the shoulders 39 and above the converging side walls 26 of the base 42, in the area above the notch 28. A set of elongated slots 44 are formed in the gate 14 to fit over the front sockets 38 and allow the gate 14 to move forward and backward between a first and second position. A resilient member 46 biases the gate 14 into the normally retracted second position.

When the dispenser is not in use, a forward member 48 of the gate 14 is disposed between the hole 12 and the notch 28 of the recess 30. A rear edge 52 of the forward member 48 abuts against the sockets 38 under the action of the biasing member 4. With the forward member 48 disposed between the hole 12 and notch 28, access to the washers 18 through the hole 12 is effectively blocked (FIG. 5). Further, with the hole 12 blocked, the washers 18 may not accidentally fall out of the dispenser during shipping or handling.

When a dental washer 18 is needed, a user grasps the dispenser 10 and tilts the recess 30 of the dispenser 10 towards the notch 28. Tilting the dispenser 10 towards the notch 28 causes a washer 18 to slide into the notch 28. The user pushes the gate 14 forward (as shown by the arrow 50 of FIG. 1). The forward motion 50 of the gate 14 causes the rear edge 54 of the forward member 48 to abut against the sockets 38 from the other direction to define a fully extended position. In the fully extended position, the hole 16 and hole 12 are both in coaxial registration with the notch 28. With the hole 16 of the gate 14 and the hole 12 of the top plate 20 in registration, access may be gained to the notch 28 and to a washer 18 within the notch 28.

Specific embodiments of a novel apparatus for dispensing dental washers according to the present invention have been described for the purpose of illustrating the manner in which the invention is made and used. It should be understood that the implementation of other variants and modifications of the invention and its various aspects will be apparent to one skilled in the art, and that the invention is not limited to the specific embodiments described. Therefore, it is contemplated to cover by the present invention and all modifications, variations, or equivalents that fall within the true spirit and scope of the basic underlying principles disclosed and claimed herein.

I claim:

1. An apparatus for dispensing washers for controlling a depth of penetration of a reamer during root canals, such apparatus comprising:

a body including a recess for storing a plurality of washers to be positioned on the reamer;

a washer access door with an aperture, mounted on said body, said recess having oppositely disposed stationary side walls which converge at a notch at a location proximate said access door with top and bottom walls bounding said notch; and an aperture and a passageway formed in said top wall above said notch for receiving said access door within the passage way between the top wall and recess, the access door being slidably movable between a first position in which the aperture of the top wall and aperture of the access door are in registration with the notch to permit a washer within the notch to be engaged by said reamer, and a second position.

2. The apparatus as in claim 1 further comprising a resilient member for resiliently biasing the access door into the second position.

3. The apparatus as in claim 1 wherein the apertures in the top wall and access door further comprise a diameter greater than that of the washers.

4. The apparatus as in claim 1 further comprising a third aperture in the bottom wall of the notch in coaxial alignment with the aperture of the top wall.

5. The apparatus as in claim 1 further comprising a tab disposed on an exterior of the body for biasing the access door from the second position to the first position.

6. The apparatus as in claim 1 wherein the recess further comprises the oppositely disposed side walls and top and bottom walls.

7. The apparatus as in claim 1 wherein the recess communicates with the notch provided in such body, the height of said notch corresponding substantially to the thickness of said washers so that, when the washers are moved from the recess into said notch, they do not overlap one another in the notch, but are juxtaposed therein.

8. The apparatus as in claim 1 further comprising a gradual convergence of the side walls so that upon tilting the body the washers are caused to enter the notch.

9. An apparatus for dispensing washers for controlling a depth of penetration of a reamer during root canals, such apparatus comprising:

a body including two spaced apart planar elements in substantially parallel relationship;

opposing stationary side walls between the spaced apart planar elements perpendicular to the planar elements, enclosing a recess within the body and converging towards one edge of the two spaced apart planar elements to form a notch around an axis of a first aperture in a first planar element of the two spaced apart planar elements;

a passageway disposed in the first planar element between the first spaced apart planar element and the notch; and a slidable access door having a second aperture, disposed in the passageway and slidable between a first access door position in which the aperture in the first planar element and aperture of the access door are in registration with the notch to permit a washer within the notch to be engaged by said reamer, and a second access door position where the aperture of the top planar element is blocked by the access door.

10. The apparatus as in claim 9 wherein the first and second apertures are of a diameter greater than that of the washers.

11. The apparatus as in claim 9 further comprising a third aperture in the second planar element of the two spaced apart planar element in coaxial alignment with the first aperture.

12. The apparatus as in claim 9 further comprising a resilient member for resiliently biasing the access door into the second position.

13. The apparatus as in claim 9 further comprising a tab disposed on an exterior of the body for biasing the access door from the second position to the first position.

14. The apparatus as in claim 9 wherein the recess further comprises the oppositely disposed side walls and top and bottom walls.

15. The apparatus as in claim 9 wherein the recess communicates with the notch provided in such body, the height of said notch corresponding substantially to the thickness of said washers so that, when the washers are moved from the recess into said notch, they do not overlap one another in the notch, but are juxtaposed therein.

16. The apparatus as in claim 9 further comprising a gradual convergence of the side walls so that upon tilting the body the washers are caused to enter the notch.

* * * * *